(12) United States Patent
Choi et al.

(10) Patent No.: US 9,429,516 B2
(45) Date of Patent: Aug. 30, 2016

(54) DEVICE FOR OPTICAL COHERENCE TOMOGRAPHY

(71) Applicant: KOREA UNIVERSITY RESEARCH AND BUSINESS FOUNDATION, Seoul (KR)

(72) Inventors: Wonshik Choi, Seoul (KR); Sungsam Kang, Seoul (KR); Seungwon Jeong, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 14/657,500

(22) Filed: Mar. 13, 2015

(65) Prior Publication Data

US 2016/0061725 A1  Mar. 3, 2016

(30) Foreign Application Priority Data

Sep. 3, 2014 (KR) .................. 10-2014-0116862

(51) Int. Cl.
*G01B 9/02* (2006.01)
*G01N 21/47* (2006.01)

(52) U.S. Cl.
CPC ....... *G01N 21/4795* (2013.01); *G01B 9/02032* (2013.01); *G01B 9/02091* (2013.01); *G01B 2290/65* (2013.01)

(58) Field of Classification Search
CPC  G01B 9/02; G01B 11/2441; G01N 21/4795; A61B 5/0066; A61B 3/102
USPC ........................................ 356/497
See application file for complete search history.

(56) References Cited

U.S. PATENT DOCUMENTS

| | | | | |
|---|---|---|---|---|
| 4,715,684 A | * | 12/1987 | Gagnon | H04N 9/3167 348/E9.027 |
| 5,418,380 A | * | 5/1995 | Simon | G02B 27/288 250/550 |
| 6,082,861 A | * | 7/2000 | Dove | G02B 27/1026 348/E9.027 |

(Continued)

FOREIGN PATENT DOCUMENTS

JP    2008157710 A    7/2008

OTHER PUBLICATIONS

Youngwoon Choi et al. "Full-field and single-shot quantitative phase microscopy using dynamic speckle illumination". Optics Letters. vol. 36, No. 13, pp. 2465-2467, Jul. 1, 2011.

(Continued)

*Primary Examiner* — Tarifur Chowdhury
*Assistant Examiner* — Md M Rahman
(74) *Attorney, Agent, or Firm* — Sughrue Mion, PLLC (57) ABSTRACT

A device for optical coherence tomography (OCT) is provided. The device includes a light source for generating a sample beam incident on a matter and a reference beam for creating interference with the sample beam; a spatial light modulator enabling a plurality of ramp patterns for controlling an incident angle of the sample beam; and a diffraction grating for transmitting only a first diffraction component of the reference beam; whereby an image of the matter within a medium is captured by generating an interference image formed by the interference between the sample beam and the reference beam.

3 Claims, 6 Drawing Sheets

(56) References Cited

U.S. PATENT DOCUMENTS

| | | | | |
|---|---|---|---|---|
| 6,816,290 B2* | 11/2004 | Mukawa | ............... | G02B 5/32 |
| | | | | 348/E9.027 |
| 7,253,934 B2* | 8/2007 | Toishi | ............... | G03H 1/02 |
| | | | | 359/22 |
| 8,143,600 B2* | 3/2012 | Seibel | ............... | G01N 21/4795 |
| | | | | 250/461.2 |
| 9,213,312 B2* | 12/2015 | Pyun | ............... | G03H 1/0476 |
| 2009/0161090 A1* | 6/2009 | Campbell | ............... | A61B 3/0091 |
| | | | | 356/3 |
| 2009/0208072 A1* | 8/2009 | Seibel | ............... | G01N 21/4795 |
| | | | | 382/128 |
| 2011/0149239 A1* | 6/2011 | Neal | ............... | A61B 3/0025 |
| | | | | 351/205 |
| 2013/0100525 A1* | 4/2013 | Chiang | ............... | G02B 21/082 |
| | | | | 359/385 |
| 2013/0215730 A1* | 8/2013 | Okamoto | ............... | G11B 7/0065 |
| | | | | 369/103 |
| 2016/0061725 A1* | 3/2016 | Choi | ............... | G01N 21/4795 |
| | | | | 356/497 |

OTHER PUBLICATIONS

Moonseok Kim et al. "Maximal energy transport through disordered media with the implementation of transmission eigenchannels". nature photonics. vol. 6, pp. 581-586, Jul. 22, 2012.

Youngwoon Choi et al., "Measurement of the Time-Resolved Reflection matrix for Enhancing Light Energy Delivery into a Scattering Medium," Physical Review Letters. PRL 111, 243901-1-243901-5, Dec. 13, 2013.

* cited by examiner

DEVICE FOR OPTICAL COHERENCE TOMOGRAPHY

CROSS-REFERENCE TO RELATED APPLICATIONS

This application claims priority under 35 U.S.C. § 119(a) to Korean Patent Application No. 10-2014-0116862 filed on Sep. 3, 2014, the disclosure of which is incorporated by reference in its entirety herein.

BACKGROUND

1. Field

The present invention generally relates to a device for optical coherence tomography (OCT) and particularly, to a device, among others as described, for a high resolution tomography of an internal scattering medium based on a collective accumulation of single scattering (CASS) microscopy.

2. Description of Related Art

Recently, a development has been underway for an optical coherence topography (OCT) device having a design simpler than that of a computerized or computed tomography (CT) device or a magnetic resonance imaging (MRI) device and resolution higher than that of an ultrasound imaging device. An OCT device directs low coherence light, which is close to natural light, to a multiple- or multi-scattering material, such as biological tissue, and collects reflected light to obtain a tomographic image of the biological material.

Early OCT devices constructed two-dimensional images based on a point scanning and thus, imaging of a large matter was cumbersome, as an area as large as an image to be obtained had to be scanned. A wide-field OCT device developed as an alternative is an OCT device based on an off-axis holography technique, which directs planar wave signals to a matter and a reference mirror and gives an angle to a reference beam, so as to make the beam obliquely incident to a camera and thereby capture a tomographic image by measuring indirect signals. However, when there is a scattering medium before a target, these devices and techniques create imaging distortion due to multi-scattering within the medium.

Figure 1:
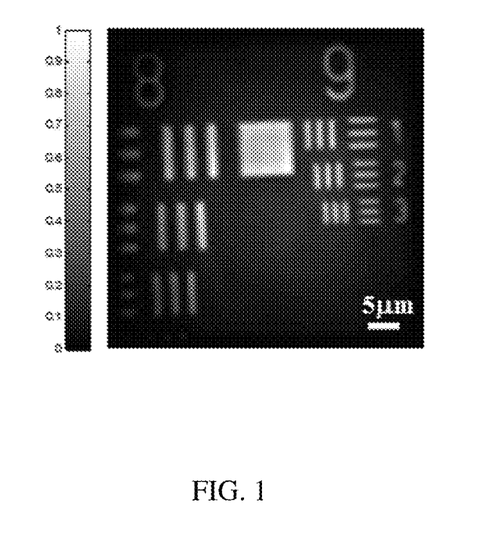
FIG. 1 is an actual image of a target captured by an optical coherence tomography device.

FIG. 1 is an actual image of a target captured by an OCT device.

Figure 2:
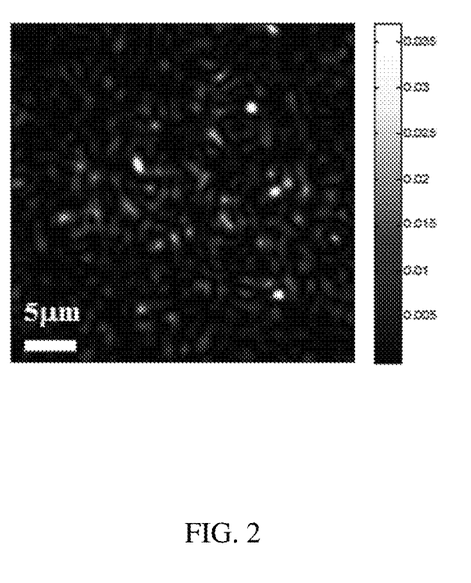
FIG. 2 is an actual image of a target captured by a conventional optical coherence tomography device, when there is a scattering medium before the target.

FIG. 2 is an actual image of a target captured by a conventional OCT device, when there is a scattering medium before the target.

As shown in FIG. 1 and FIG. 2, an image captured by an OCT device is generally an image obtained through interference signals between a light reflected from a matter and a light reflected from a reference-beam mirror; thus, only a light from a particular position in an axis-direction of the matter may be selectively covered. However, because of a medium causing much scattering within the matter, noise exists in the image, and it is difficult to verify data of a sample when the noise is strong.

Due to noise in an image captured by an OCT device, an angular compounding OCT device has been developed based on a new technique. An angular compounding OCT device captures an image of a matter by measuring an image per incident angle and cumulatively adding an intensity of the image, while changing the incident angle on the matter. Data on the matter to be obtained does not change with a change in incident angles, but as noise components change randomly, noise is reduced in the accumulated images. As such, enhanced contrast effect may be obtained.

Figure 3:
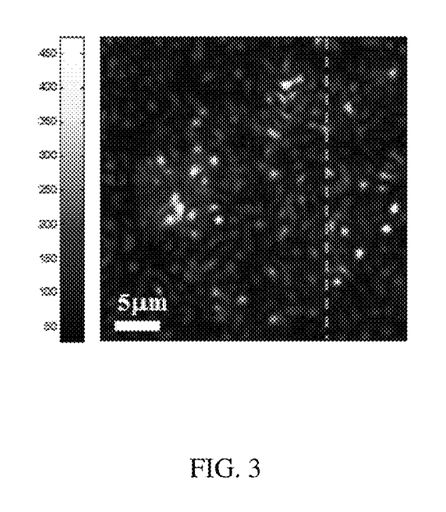
FIG. 3 is an actual image of a target captured by an angular compounding optical coherence tomography device, when there is a scattering medium before the target.

FIG. 3 is an actual image of a target captured by an angular compounding OCT device, when there is a scattering medium before the target.

However, as shown in FIG. 3, when noise intensity is relatively stronger than that of signal to be obtained due to a severity or an extent of multi-scattering, there is a limit as to image construction. For example, optical microscopy suffers from loss of resolving power in the target embedded in thick scattering media due to the dominance of strong multiple-scattered waves over the waves scattered only a single time by the target. A solution is needed to maintain full optical resolution in imaging deep within scattering media.

SUMMARY

According to an embodiment of the present invention, a device for optical coherence tomography (OCT), comprises: a light source for generating a sample beam incident on a matter and a reference beam for creating interference with the sample beam; a spatial light modulator enabling a plurality of ramp patterns for controlling an incident angle of the sample beam; and a diffraction grating for transmitting only a first diffraction component of the reference beam; whereby an image of the matter within a medium is captured by generating an interference image formed by the interference between the sample beam and the reference beam.

According to another embodiment of the present invention, a device for optical coherence tomography (OCT) comprises: a light source emitting light; a first beam splitter for separating the light emitted from the light source into a first light and a second light by transmitting or reflecting the light emitted; a spatial light modulator (SLM) for reflecting the first light emitted from the first beam splitter; a second beam splitter for reflecting the first light reflected by the spatial light modulator (SLM) and emitted at a matter and reflected by the matter; a piezoelectric transducer (PZT) for reflecting the second light emitted from the first beam splitter and controlling a travel distance of the second light; a third beam splitter for emitting the second light at a diffraction grating (DG) by reflecting the second light reflected by the piezoelectric transducer (PZT); the diffraction grating (DG) for transmitting only a first diffraction component of the second light emitted from the third beam splitter, and a camera for capturing an interference image between: the first light reflected by the second beam splitter; and the second light, with only the first diffraction component remaining, transmitted from the diffraction grating (DG); wherein an incident angle of the first light emitted at the matter is changed according to ramp pattern enabled in the spatial light modulator (SLM).

The device for optical coherence tomography (OCT), according to embodiments of the present invention, may filter multi-scattering signals, which are necessarily generated in a complex medium, when imaging a target matter within a scattering medium. Even where a potential light penetration depth is deep, the device may also construct image with high resolution corresponding to a diffraction limit. Also, the device may construct three-dimensional (3-D) image using axis scanning, as the device constructs large two-dimensional image at a given depth within the matter with one measurement.

BRIEF DESCRIPTION OF DRAWINGS

FIGS. 8a, b, and c are an actual image of another target sample captured using various techniques.

DESCRIPTION

Hereinafter, exemplary embodiments of the present invention are described with reference to the accompanying drawings. To note, the present invention is not limited to the exemplary embodiments described or a particular embodiment therein but may be implemented in various different ways. The present invention may be modified and take various other forms, without departing from the spirit and technical scope of the present invention.

Terms used herein are used only to describe specific exemplary embodiments and are not intended to limit the present invention. Terms such as "including" and "having" do not limit the present invention to features, number, step, operation, and parts or elements described; others may exist, be added or modified.

Further, unless otherwise stated, when one element is described, for example, as being "connected" or "coupled" to another element, the elements may be directly linked or indirectly linked (i.e., there may be an intermediate element between the elements). Similar concept applies to terms such as "between" and "adjacent to." Also, unless otherwise clearly stated, a singular expression includes meaning of plural expressions.

Terms such as "first" and "second" may be used to describe various parts or elements and should also not be limited to a particular part or element. The terms are used to distinguish one element from another element. For example, a first element may be designated as a second element, and vice versa, without departing from the technical scope of the present invention.

Hereinafter, exemplary embodiments of the present invention are described with reference to the accompanying drawings. To note, the term "object" as used throughout this disclosure is an imaging target for an optical coherence topography device, and "matter" comprises an actual target and scattering medium.

Figure 4:
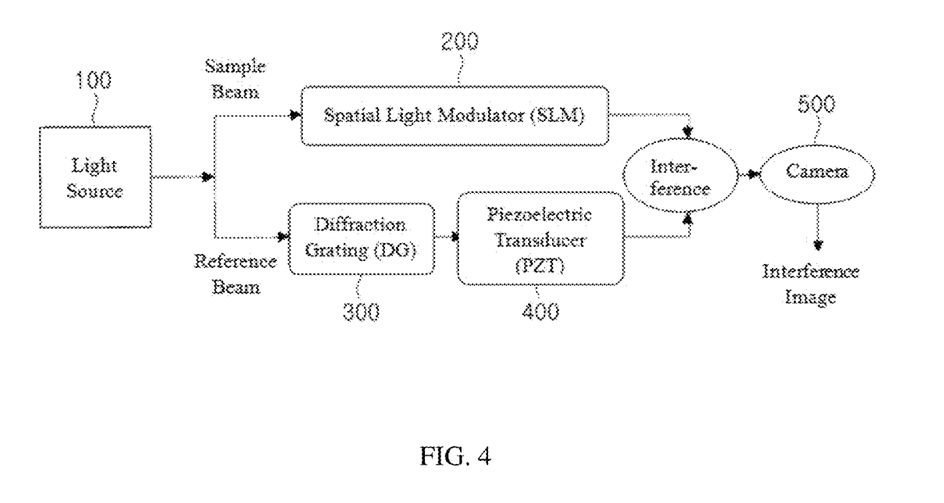
FIG. 4 is a block diagram of a device for optical coherence tomography, according to an embodiment.

FIG. 4 is a block diagram of a device for optical coherence tomography, according to an embodiment.

As shown in FIG. 4, the device for optical coherence tomography (OCT), according to the embodiment, comprises: a light source 100 for generating a sample beam incident on a matter and a reference beam for creating interference with the sample beam; a spatial light modulator (SLM) 200 enabling a plurality of ramp patterns for controlling an incident angle of the sample beam; and a diffraction grating (DG) 300 for transmitting only a first diffraction component of the reference beam; whereby an image of the matter within a medium is captured by generating an interference image formed by the interference between the sample beam and the reference beam.

The light source 100, which directs light at the matter, is a low-coherence light source with low coherence length. According to an embodiment, a center wavelength may be 800 nm, and a bandwidth, 25 nm; however, the center wavelength and bandwidth are not limited thereto. Also, the light source 200 is divided into a sample beam and a reference beam by a beam splitter described later. The sample beam is light, which is directed or emitted directly at the matter, and the reference beam is light, which creates interference with the sample beam reflected off the matter. Various techniques may be used applied to generate the sample beam and the reference beam from one light source.

The sample beam generated from the light source 100 is incident on or emitted at the spatial light modulator 200. The spatial light modulator 200 reflector comprises a plurality of spatial light/optical modulation elements having an aperture or a reflector. The spatial light modulator 200 reflector modulates light incident on the aperture or the reflector of the spatial light/optical modulation elements by transmitting or reflecting the light.

According to an embodiment, a plurality of ramp patterns may be enabled in the spatial light modulator 200. The incident angle of the sample beam is controlled according to each of the plurality of ramp patterns. Here, a quantity of the plurality of ramp patterns may be determined by a center wavelength of the light source 100. According to an embodiment, the quantity may be determined based on a diffraction limit, which is determined by a numerical aperture of an objective lens installed in the spatial light modulator 200.

The diffraction grating 300 may be denoted as multiple parallel lines cut on a plane glass or concave metal plate at an equidistant interval, where numerous slots are made at regular intervals. When light is directed or emitted, a spectrum may be obtained as a transmitted or reflected light is dispersed into light components by wavelengths. The diffraction grating 300 absorbs or scatters a light emitted in a parallel direction at the lines and transmits a light emitted through the slot where there are not any lines. The transmitted light does not advance but is diffracted and dispersed in a cylindrical form, according to Huygens's principle.

According to an embodiment, an interval between gratings in the diffraction grating 300 may be from 10 μm to 20 μm, and in more detail, from 13 μm to 14 μm.

Of the reference beam transmitted through the diffraction grating 300, only a first diffraction component is permitted to create interference with the sample beam reflected from the matter and directed or emitted at a camera 500. When using the first diffraction component of the reference beam transmitted through the diffraction grating 300, one scanning or imaging is needed, unlike in a phase shift holography technique. Further, unlike a simple off-axis holography technique, an interference image with uniform interference intensity may be acquired over a wide area, and thus, quality of wide-field imaging may be increased.

According to an embodiment, the device for optical coherence tomography (OCT) further comprises a piezoelectric transducer (PZT) 400. The piezoelectric transducer 400 is a device for controlling a travel distance of the reference beam. The piezoelectric transducer 400 may control a depth of the matter at which the sample beam is directed or emitted, by controlling the travel distance of the reference beam.

Hereinafter, actual operation of the device for optical coherence tomography (OCT) and imaging results thereof are described through an experimental example.

Figure 5:
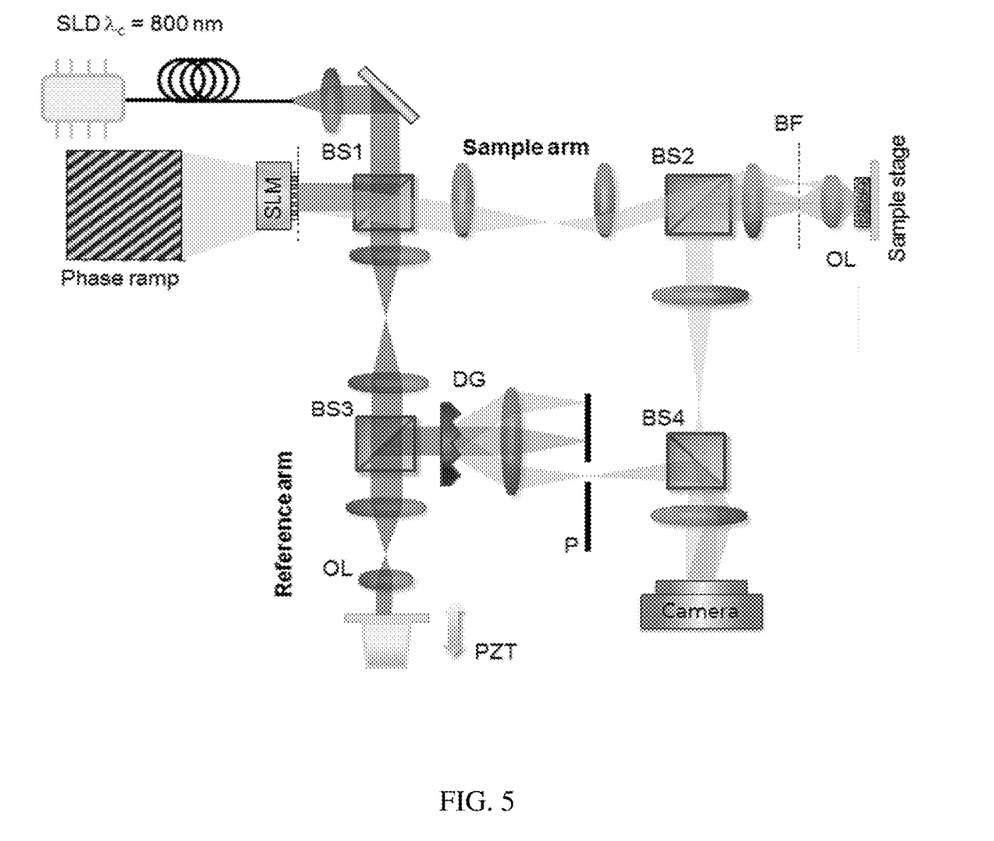
FIG. 5 is an experimental setup for an exemplary experiment for the device for optical coherence tomography, according to an embodiment.

FIG. 5 is an experimental setup for an exemplary experiment for the device for optical coherence tomography, according to an embodiment. In the exemplary experiment, a method based on a collective accumulation of single scattering (CASS) microscopy is also described.

As shown in FIG. 5, a device for optical coherence tomography, according to an embodiment, comprises: a light source emitting light; a first beam splitter (BS1) for separating the light emitted from the light source into a first light and a second light by transmitting or reflecting the light emitted; a spatial light modulator (SLM) for reflecting the first light emitted from the first beam splitter (BS1); a second beam splitter (BS2) for reflecting the first light reflected by the spatial light modulator (SLM) and emitted at a matter and reflected by the matter; a piezoelectric transducer (PZT) for reflecting the second light emitted from the first beam splitter (BS1) and controlling a travel distance of the second light; a third beam splitter (BS3) for emitting the second light at a diffraction grating (DG) by reflecting the second light reflected by the piezoelectric transducer (PZT); the diffraction grating (DG) for transmitting only a first diffraction component of the second light emitted from the third beam splitter (BS3), and a camera for capturing an interference image between: the first light reflected by the second beam splitter (BS2); and the second light, with only the first diffraction component remaining, transmitted from the diffraction grating (DG); wherein an incident angle of the first light emitted at the matter is changed according to ramp pattern enabled in the spatial light modulator (SLM). Here, the first light is the sample beam, and the second light is the reference beam described earlier.

To describe the experimental setup in more detail, as the light source, a super luminescent diode (SLD) with a center wavelength of 800 nm and bandwidth of 25 nm is used. A Mach-Zhender Interferometer is also used. In a path of a sample beam, the spatial light modulator (SLM) controls the incident angle of the sample beam by enabling the ramp patterns. A beam from the light source is divided by the first beam splitter (BS1) and a reflected beam is emitted at the spatial light modulator (SLM). A beam reflected by the spatial light modulator (SLM) is used as the sample beam, and a beam transmitted by the first beam splitter (BS1) is used as the reference beam. The diffraction grating (DG) is positioned in an image plane in a path of the reference beam and only the first diffraction component of the transmitted beam is emitted at the camera. When a path difference between a first component of the reference beam and the sample beam is reduced to within a coherence distance approximately 10 μm, and simultaneously emitted at a camera, an off-axis holography image may be obtained. Through this image, intensity of the sample beam and a phase image may be obtained. Sample data thus obtained is an interference image through low-coherence interferometer using broadband wavelength and is thus, a time-gated or time-resolved reflective image.

A sample of the matter, which was prepared for the exemplary experiment, is a USAF (United States Air Force) target layered with a polymer material (PDMS) having Polystyrene particles having a 1 μm diameter. Optical characteristics of such sample are 100 μm for average scattering distance and 1 mm for an average transmission distance or transport mean free path—which are very similar to optical characteristic of biological tissue.

In the experiment, a spatial input-output correlation is used in order to further enhance a detection of single-scattered waves. Specifically, in the experiment, it is noted that an input-output response for single scattering preserves in-plane momentum, while that for multiple scattering waves does not.

To clarify, considering a thin periodic structure with wave vector $\vec{k}^s$ in reciprocal space: for single scattering, an in-plane wave vector of a reflected wave $\vec{k}_\parallel^r$, which is a wave vector projected to a sample (x, y) plane, is an addition of $\vec{k}^s$ to the in-plane wave vector of an incident wave $\vec{k}_\parallel^i$, regardless of an incident wave vector. As described below, in the experiment, a map of reflected waves for $N_{tot}$=2500 different incident wave vector is measured and constructed. For example, by coherently adding relative complex amplitudes for pairs of input-output waves with a same momentum difference ($\vec{k}^s=\vec{k}_\parallel^r-\vec{k}_\parallel^i$), single-scattered waves associated with a $\vec{k}^s$ component of an object function may be collectively accumulated, as described later. This leads to an enhancement of single scattering intensity to an order of $N_{tot}^2$.

In the experiment, the quantity ($N_A$) of the ramp patterns is 2500, and the incident angle of the sample beam changes 2500 times, per each of the ramp patterns. The camera captures a quantity of 2500 interference images (raw-data) for interference per each incident angle.

The 2500 interference images (raw-data) obtained through the experimental example are expressed in a field-map of a sample (x, y) plane, according to Formula (1).

$$u(x, y; \vec{k}_\parallel^i, \tau) \tag{1}$$

$\vec{k}_\parallel^i$ denotes an incident angle on a sample, and $\tau$ denotes a travel time of a beam. Formula (2) is a Fourier transformed Formula (1) (i.e., a Fourier transformation applied to Formula (1).)

$$u(\vec{k}_\parallel^r; \vec{k}_\parallel^i, \tau) \tag{2}$$

Formula (2) denotes a time resolved reflection matrix (TRRM), and $\vec{k}_\parallel^r$ denotes a reflective angle off a sample.

Figure 6:
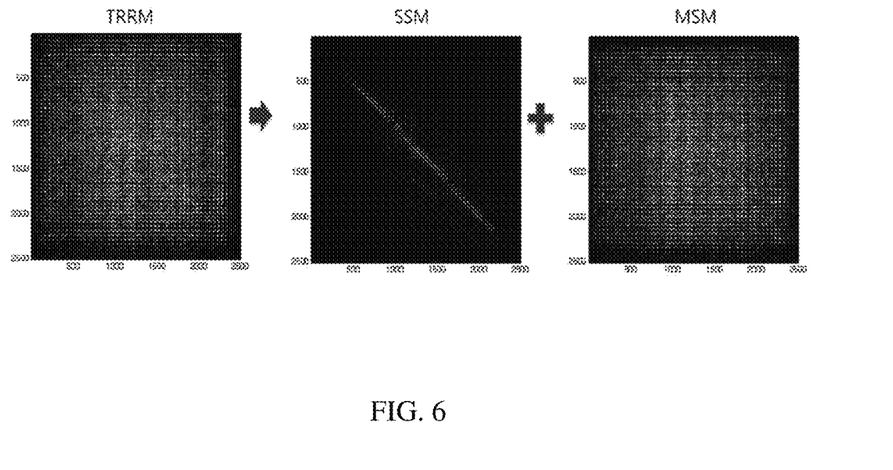
FIG. 6 is a diagram showing a time-resolved reflection matrix.

FIG. 6 is a diagram showing a time-resolved reflection matrix of a scattering medium.

As shown in FIG. 6, a time-resolved reflection matrix (TRRM) is expressed as a sum of a single-scattering matrix (SSM) and a multi-scattering matrix (MSM), according to Formula (3) below.

Since reflected waves include both single and multiple scattered waves, the time-resolved reflection matrix (TRRM), as shown in FIG. 6, is expressed as a sum of a single-scattering matrix (SSM) and a multi-scattering matrix (MSM), according to Formula (3).

$$U = U_S + U_M \tag{3}$$

When adding all diagonally oriented components in the time-resolved reflection matrix (TRRM) shown in FIG. 6, each of the components (in the time-resolved reflection matrix (TRRM)) is stacked in a same phase as all indicating a same spectrum, and each component of the multi-scattering matrix (MSM) is added to a random phase. That is, as a number of added components increases, relative size of single-scattering components relative to multi-scattering components increases, and in effect, decreases image distortion due to multi-scattering.

Here, a function for a matter of an actual target is denoted as $f(x, y)$, and a Fourier transformed $f(x, y)$ is $F(\vec{k}^s)$. A wave vector $\vec{k}^s = (k_x^s, k_y^s)$ denotes a target's spatial frequency in a sample $(x, y)$ plane. A relationship between the single-scattering matrix (SSM) and $f(x, y)$ as Fourier transformed are shown, according to Formula (4).

$$U_S(\vec{k}_\parallel^r; \vec{k}_\parallel^i) \approx F(\vec{k}_\parallel^r - \vec{k}_\parallel^i) = F(\vec{k}^s) \quad (4)$$

A relational expression such as Formula (4) is not applicable to a multi-scattering matrix (MSM), $U_M$, because there is no relational association, as in single-scattering matrix (SSM), between multi-scattering waves with each different incident angles.

Using this difference, each component of the matrix is added according to the Formula (5).

$$\sum_{\vec{k}_\parallel^i} \mathcal{U}(\vec{k}_\parallel^r; \vec{k}_\parallel^i) \approx N(\vec{k}^s) \mathcal{F}(\vec{k}^s) + \sum_{\vec{k}_\parallel^i} \mathcal{U}_M \quad (5)$$

$N(\vec{k}^s)$ denotes a quantity of components included in a sum or aggregate. According to Formula (5), signal strength of the single-scattering matrix (SSM) is increased relative to ($\vec{k}^s$), and signal strength of the multi-scattering matrix (MSM) is increased relative to $N(\vec{k}^s)$.

Eventually, signal strength of multi-scattering waves becomes a negligible value in relation to signal strength of single-scattering waves.

Computing $f(x, y)$ based on an inverse Fourier transformation of $F(\vec{k}^s)$ derived from results of Equation (4) and Equation (5), a function for a two-dimensional cross section is obtained of a target in an actual sample prepared for imaging.

Figure 7:
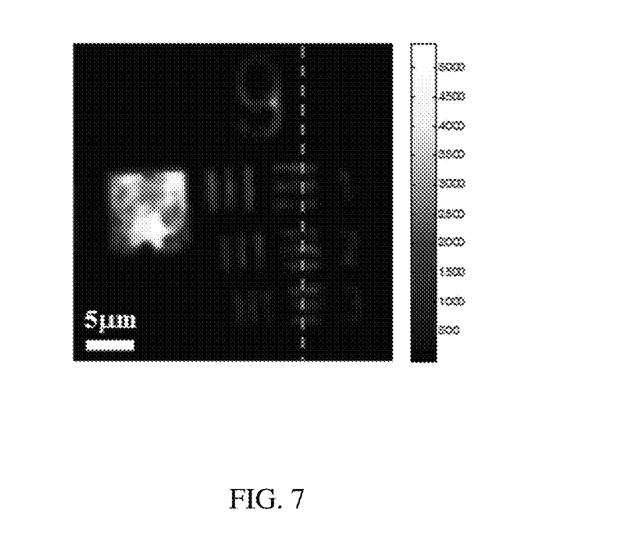
FIG. 7 is an actual enlarged image of a target captured using the experimental setup in FIG. 5.

FIG. 7 is an actual enlarged image of a target captured using the experimental setup in FIG. 5, according to an embodiment.

Comparing the image in FIG. 7 with the images in FIG. 2 and FIG. 3, which are blurry due to strong noise, it may be verified that the actual enlarged image of a target captured using the device for optical coherence tomography (OCT), according to an embodiment of the present invention, is sharp and clear with almost no noise effect.

Figure 8A:
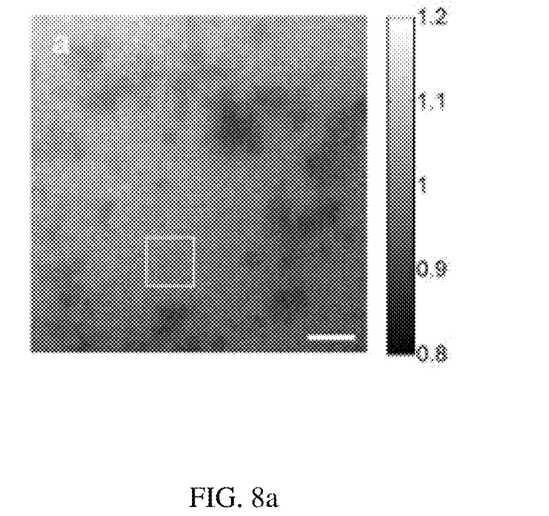
FIG. 8a is a conventional bright field image captured with the light source illuminating the sample from a backside.
Figure 8B:
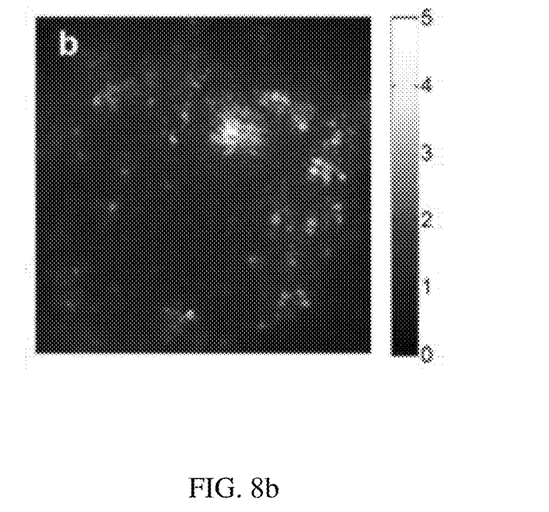
FIG. 8b is a conventional angular compounding image for the same sample.
Figure 8C:
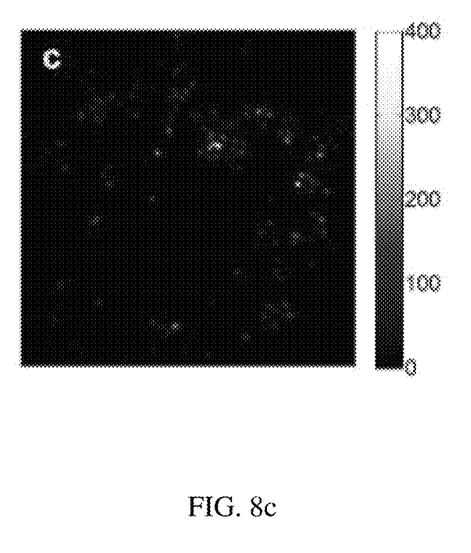
FIG. 8c is an image of the same sample captured using a setup similar to the experimental setup in FIG. 5, according to an embodiment.

FIGS. 8a, b, and c are an actual image of another target sample captured using various techniques. FIG. 8a is a conventional bright field image captured with the light source (LED) illuminating the sample from a backside. FIG. 8b is a conventional angular compounding image for the same sample. FIG. 8c is a CASS microscopy image of the same sample captured using a setup similar to the experimental setup in FIG. 5, according to an embodiment. In FIGS. 8a, b, and c, scales (scale bar 10 μm) are normalized by a background region containing no beads as indicated by a white box in FIG. 8a.

A target sample of the matter, which was prepared for this exemplary experiment, is inhomogeneous biological tissue: gold-coated silica beads of 2 μm diameter, which are sandwiched between two slices of 560 μm-thick tissues of a rat's brain.

Comparing the CASS microscopy image in FIG. 8c with the images in FIG. 8a and FIG. 8b, it may be verified that the bright field image with LED illuminated from the backside of the sample (FIG. 8a) and the angular compounding image (FIG. 8b) cannot identify the individual gold-coated silica beads, while the CASS microscopy image (FIG. 8c) clearly does—thereby confirming superior resolving power of the method based on a collective accumulation of single scattering (CASS) microscopy over the conventional methods.

In the exemplary experiment, the CASS microscopy method of collectively enhancing single-scattered waves from a target object embedded in thick scattering media is described. Both a time resolved detection and a spatial input-output correlation are used to identify those reflected waves that conserve in-plane momentum, which is a property of the single-scattered waves. By implementing a super radiance-like collective accumulation of the single-scattered waves, single scattering signals to multiple scattering background ratio is enhanced by more than three orders of magnitude. Furthermore, optical microscopic imaging is achieved, for example, with up to a depth of 11.5 times a scattering mean free path and with near-diffraction-limit resolution of 1.5 μm, representing more than a tenfold increase in imaging depth over conventional imaging.

Consequently, the method of high-resolution imaging at an unprecedented target depth will lead to advances in life science and biomedical fields, in which a shallow imaging depth of conventional imaging devices and techniques poses a major obstacle. In addition, as described herein, an ability to distinguish single and multiple-scattered waves will open new venues in the study of physics for interaction between light and complex media.

The foregoing description concerns exemplary embodiments of the present invention, which are intended to be illustrative, and should not be construed as limiting the present invention. Many modifications and variations may be made without departing from the spirit and scope of the present invention, as will be readily apparent to persons skilled in the art and as claimed below.

The invention claimed is:

1. A device for optical coherence tomography (OCT), comprising:
   a light source for emitting light;
   a first beam splitter for separating the light emitted from the light source into a first light and a second light by transmitting or reflecting the light emitted;
   a spatial light modulator (SLM) for reflecting the first light emitted from the first beam splitter;
   a second beam splitter for reflecting the first light reflected by the spatial light modulator (SLM) and emitted at a matter and reflected by the matter;
   a piezoelectric transducer (PZT) for reflecting the second light emitted from the first beam splitter and controlling a travel distance of the second light;
   a third beam splitter for emitting the second light at a diffraction grating (DG) by reflecting the second light reflected by the piezoelectric transducer (PZT);
   the diffraction grating (DG) for transmitting only a first diffraction component of the second light emitted from the third beam splitter, and
   a camera for capturing an interference image between:
      the first light reflected by the second beam splitter; and
      the second light, with only the first diffraction component remaining,
   transmitted from the diffraction grating (DG);
   wherein an incident angle of the first light emitted at the matter is changed according to ramp pattern enabled in the spatial light modulator (SLM).

2. The device for optical coherence tomography (OCT) according to claim 1, wherein the piezoelectric transducer (PZT) reduces a path difference between the first light and the first diffraction component of the second light to less than 10 μm.

3. The device for optical coherence tomography (OCT) according to claim 1, further comprising
a fourth beam splitter for:
emitting the second light, with only the first component remaining, at a camera; and
emitting the first light at the camera by transmitting the first light.

\* \* \* \* \*